(12) United States Patent
Fu et al.

(10) Patent No.: US 10,705,093 B2
(45) Date of Patent: Jul. 7, 2020

(54) DETERMINATION OF SMALL-MOLECULE THIOLS AND DISULFIDES: PROTEIN BOUND CYS AND TOTAL CYSTEINE AS BIOMARKERS OF OXIDATIVE STRESS

(71) Applicant: Bloodworks, Seattle, WA (US)

(72) Inventors: Xiaoyun Fu, Kenmore, WA (US); Shelby A. Cate, Seattle, WA (US); Jose Aron Lopez, Seattle, WA (US); Junmei Chen, Seattle, WA (US); Barbara A. Konkle, Seattle, WA (US)

(73) Assignee: Bloodworks, Seattle, WA (US)

( * ) Notice: Subject to any disclaimer, the term of this patent is extended or adjusted under 35 U.S.C. 154(b) by 502 days.

(21) Appl. No.: 15/328,694

(22) PCT Filed: Jul. 27, 2015

(86) PCT No.: PCT/US2015/042318
§ 371 (c)(1),
(2) Date: Jun. 14, 2017

(87) PCT Pub. No.: WO2016/015060
PCT Pub. Date: Jan. 28, 2016

(65) Prior Publication Data
US 2017/0219598 A1    Aug. 3, 2017

Related U.S. Application Data

(60) Provisional application No. 62/029,366, filed on Jul. 25, 2014.

(51) Int. Cl.
*G01N 33/68* (2006.01)
*A61K 9/00* (2006.01)
(Continued)

(52) U.S. Cl.
CPC ....... *G01N 33/6815* (2013.01); *A61K 9/0019* (2013.01); *A61K 9/0053* (2013.01);
(Continued)

(58) Field of Classification Search
CPC ....... G01N 33/6815; G01N 2800/7009; G01N 2030/8813; A61K 9/0053; A61K 9/0019;
(Continued)

(56) References Cited

U.S. PATENT DOCUMENTS

| | | | |
|---|---|---|---|
| 5,387,421 A | 2/1995 | Amidon et al. | |
| 5,998,191 A * | 12/1999 | Tan ...................... | C12N 9/0051 435/232 |

(Continued)

FOREIGN PATENT DOCUMENTS

| | | |
|---|---|---|
| WO | WO 2000/064421 A2 | 11/2000 |
| WO | WO 2006/004736 A2 | 1/2006 |
| WO | WO 2008/019060 A2 | 2/2008 |

OTHER PUBLICATIONS

Dalle-Donne, et al., "Biomarkers of Oxidative Damage in Human Disease," Clin. Chem., vol. 52, No. 4, 2006, pp. 601-623.
(Continued)

*Primary Examiner* — Lore R Jarrett
(74) *Attorney, Agent, or Firm* — Lee & Hayes PC; C. Rachal Winger; Thu Nguyen

(57) ABSTRACT

Compositions and methods for determining the level of thiol and disulfide containing molecules in a sample are provided. The compositions and methods can be used to determine the level of oxidative stress in a subject with or without antioxidant treatment. Also provided are biomarkers of oxidative stress.

20 Claims, 7 Drawing Sheets

(51) Int. Cl.
A61K 31/19 (2006.01)
G01N 30/88 (2006.01)
(52) U.S. Cl.
CPC ...... *A61K 31/19* (2013.01); *G01N 2030/8813* (2013.01); *G01N 2800/7009* (2013.01)
(58) Field of Classification Search
CPC .. A61K 31/19; C12Q 1/26; C12Q 1/34; Y10S 435/975; Y10S 435/968
See application file for complete search history.

(56) References Cited

U.S. PATENT DOCUMENTS

| | | | | |
|---|---|---|---|---|
| 7,135,306 | B2* | 11/2006 | Esaki | C12N 9/1007 435/18 |
| 8,669,110 | B2 | 3/2014 | Dehal et al. | |
| 2002/0123088 | A1* | 9/2002 | Matsuyama | C12Q 1/26 435/18 |
| 2004/0229815 | A1 | 11/2004 | Nagasawa et al. | |
| 2006/0199280 | A1* | 9/2006 | Bar-Or | G01N 33/68 436/518 |
| 2008/0261315 | A1* | 10/2008 | Strongin | G01N 33/6815 436/86 |
| 2012/0142550 | A1* | 6/2012 | Zehnder | G01N 33/6893 506/9 |

OTHER PUBLICATIONS

Dalle-Donne, et al., "Molecular Mechanisms and Potential Clinical Significance of S-Glutathionylation," Antioxid. Redox Signal., vol. 10, No. 3, 2008, pp. 445-473.

Rossi, et al., "Blood Glutathione Disulfide: In Vivo Factor or In Vitro Artifact?" Clin. Chem., vol. 48, No. 5, 2002, pp. 742-743.

Rossi, et al., "Oxidized Forms of Glutathione in Peripheral Blood as Biomarkers of Oxidative Stress," Clin. Chem., vol. 52, No. 7, 2006, pp. 1406-1414.

Search Report and Written Opinion dated Nov. 3, 2015 in International Application No. PCT/US2015/042318, 19 pages.

Zhu, et al.. "Determination of cellular redox status by stable isotope dilution liquid chromatography/mass spectrometry analysis of glutathione and glutathione disulfide," Rapid Commun. Mass Spectrom., vol. 22, No. 4, 2008, pp. 432-440.

PCT International Search Report and Written Opinion, International Application No. PCT/US2015/042318 dated Nov. 3, 2015, 4 pp.

Fahrenholz et al., "Molecular Speciated Isotope Dilution Mass Spectrometric Methods for Accurate, Reproducible and Direct Quantification of Reduced, Oxidized and Total Glutathione in Biological Samples," Analytical Chemistry, Dec. 18, 2014, vol. 87, pp. 1232-1240.

Himmelfarb et al., "Plasma Aminothiol Oxidation in Chronic Hemodialysis Patients," Kidney Int'l, Feb. 1, 2002, vol. 61, pp. 705-716.

Lou et al., "Thioltransferase is Present in the Lens Epithelial Cells as a Highly Oxidative Stress-resistant Enzyme," Experimental Eye Research, Apr. 1, 1998, vol. 66, Iss. 4, pp. 477-485.

Rajaraman, G., "Oxidative Stress: Role in Genomic Damage and Disease," Graduate School of Life Sciences, Julius-Maximillans-University of Wuerzburg, Aug. 6, 2011, Doctoral Thesis, pp. 1-143, Retrieved from the Internet: https://opus.bibliothek.uni-wuerzburg.de/files/6084/Thesis._Oli_RG.Finala4.pdf on Sep. 30, 2015.

Winyard, P., et al., "Determination of S-Nitrosothiols in Biological and Clinical Samples Using Electron Paramagnetic Resonance Spectrometry with Spin Trapping," Methods in Enzymology, Feb. 1, 2008, vol. 441, pp. 151-160.

Zhu et al., "Determination of Cellular Redox Status by Stable Isotope Dilution Liquid Chromatography/Mass Spectrometry Analysis of Glutathione and Glutathione Disulfide," Rapid Communications in Mass Spectrometry, Feb. 1, 2008, vol. 22, Iss. 4, pp. 432-440.

Blair, I.A., "Analysis of Endogenous Glutathione-Adducts and Their Metabolites," Biomed Chromatogr., Jan. 2010, pp. 29-38, vol. 24, No. 1.

Ciccimaro, E. et al., "Stable-Isotope Dilution for LC-MS for Quantitative Biomarker Analysis," Bioanalysis, Feb. 2010, pp. 311-341, vol. 2, No. 2.

Moore, T. et al., "A New LC-MS/MS Method for the Clinical Determination of Reduced and Oxidized Glutathione from Whole Blood," Journal of Chromatography B, 2013, pp. 51-55, vol. 929.

New, L-S. et al., "Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma," Journal of Chromatographic Science, Mar. 2008, pp. 209-214, vol. 46.

Winnick, W. et al., "Measurement of Oxidative Stress Parameters Using Liquid Chromatography-Tandem Mass Spectroscopy (LC-MS/MS)," Toxicology and Applied Pharmacology, Nov. 2008, pp. 100-106, vol. 233.

* cited by examiner

DETERMINATION OF SMALL-MOLECULE THIOLS AND DISULFIDES: PROTEIN BOUND CYS AND TOTAL CYSTEINE AS BIOMARKERS OF OXIDATIVE STRESS

FIELD

The invention relates to compositions and methods for determining the levels of thiol and disulfide containing molecules in a sample as indicators of oxidative stress.

BACKGROUND

Increasingly, oxidative stress has been implicated in a variety of disease states, leading widespread interest in determining relevant biomarkers for evaluation of oxidative stress. Glutathione (GSH) is a tripeptide of glutamic acid, cysteine, and glycine, with a gamma-glutamyl linkage between Cys and Glu and the free Cys sulfhydryl as the functionally active component. GSH acts as an antioxidant to protect cells or tissues from oxidation by reactive oxygen/nitrogen species. Upon exposure to oxidative conditions, GSH is oxidized to form glutathione disulfide (GSSG), which can be subsequently converted back to GSH by glutathione reductase. An increased GSH-to-GSSG ratio has been used as a sensitive biomarker to evaluate extent of oxidative stress [1, 2]. Most commercially available GSH/GSSG assay kits are based on enzymatic recycling methods [3]. The variation of the quantification is high due to high susceptibility of GSH to artificial oxidation during the performance of the assay. For example, one group reported that the mean values obtained for GSH and GSSG among thirty studies spanned two orders of magnitude [3]. Furthermore, GSH is mostly utilized as an intracellular antioxidant, so the ratio of GSH/GSSH can be used to assess oxidative state in whole blood or red blood cell samples. However, the substantially lower extracellular concentration of GSH/GSSG makes it a much less sensitive indicator for other types of samples such as plasma. Protein bound GSH has long been considered an indicator of oxidative stress in whole blood [4] [5], but much less attention is paid to protein bound Cysteine. The reason, at least, in part, is the lack of a sensitive and high throughput assay to determine it.

Thus, more reliable and sensitive assays for determining the level of oxidation of thiol and disulfide containing molecules in a sample are needed that can be used for a variety of patient samples, including plasma. Furthermore, finding plasma biomarkers of thiol oxidation are needed for evaluation of a wide range of disease status with oxidative stress and to evaluate response to antioxidants treatment. The present disclosure satisfies these and other needs.

SUMMARY

Disclosed herein is an ultra-performance (UP) LC-MS/MS method with Multiple Reaction Monitoring (MRM) to determine the level of thiol and disulfide containing molecules in a sample.

In a first aspect, disclosed herein is a method for determining the level of thiol and disulfide containing molecules in a sample, the method comprising: a) treating a sample with a reagent to prevent free thiol oxidation; (ii) adding an isotopically labeled analogue of each molecule of interest; and (iii) adding methanol to extract the molecules; b) subjecting the sample to liquid chromatography-tandem mass spectrometry (LC-MS/MS) with Multiple Reaction Monitoring (MRM) to determine the levels of reduced and oxidized forms of thiol and disulfide containing molecules in the sample, wherein the thiol and disulfide containing molecules are at least one of: GSH, GSSG, cysteine, cystine, N-acetyl-cysteine (NAC), N-acetyl-cystine (NACss), Cys-Gly(CG), gamma-GluCys (γEC), homocysteine(Hcy), homocytine, Cys-ss-GSH, Cys-ss-NAC, Cys-ss-Hcy, Cys-ss-CG, Cys-ss-γEC, GSH-ss-NAC, CGss, γECss, Protein-ss-Cys (p-ss-Cys), Protein-ss-GSH (p-ss-GSH), Protein-ss-NAC (p-ss-NAC), Protein-ss-Hcy (p-ss-Hcy), or Protein-ss-CG.

In a second aspect, disclosed herein for determining oxidative stress in a subject, the method comprising: a) treating a sample from a subject with a reagent to prevent free thiol oxidation; (ii) adding an isotopically labeled analogue of each molecule of interest; and (iii) adding methanol to extract the molecules; b) subjecting the sample to liquid chromatography-tandem mass spectrometry (LC-MS/MS) with Multiple Reaction Monitoring (MRM) to determine the levels of reduced and oxidized forms of thiol and disulfide containing molecules in the sample, wherein the thiol and disulfide containing molecules are at least one of: GSH, GSSG, cysteine, cystine, N-acetyl-cysteine (NAC), N-acetyl-cystine (NACss), CysGly (CG), gamma-GluCys, (γEC), homocysteine(Hcy), homocytine, Cys-ss-GSM Cys-ss-NAC, Cys-ss-Hcy, Cys-ss-CG, Cys-ss-γEC, GSH-ss-NAC, CGss, γECss, Protein-ss-Cys (p-ss-Cys), Protein-ss-GSH (p-ss-GSH), Protein-ss-NAC (p-ss-NAC), Protein-ss-Hcy (p-ss-Hcy), or Protein-ss-CG; and wherein a greater amount of oxidized forms of thiol and disulfide containing molecules as compared to a control is indicative of oxidative stress in the subject.

In various embodiments of the above aspects, the sample is blood or a fraction thereof, cells, or tissue. In some embodiments of the above aspects, the subject is a patient with a disease that results in oxidative stress. In some embodiments of the above aspects, the disease that results in oxidative stress is sickle cell disease (SCD), acute respiratory distress syndrome (ARDS), or thrombotic thrombocytopenic purpura (TTP).

In various embodiments of the above aspects, the levels of thiol and disulfide containing molecules in the sample are compared to a control sample from a normal healthy donor or an average value derived from samples of healthy donors.

In various embodiments of the above aspects, a greater amount of oxidized forms of thiol and disulfide containing molecules in the sample as compared to the control is indicative of oxidative stress in the subject.

In various embodiments of the above aspects, the isotopically-labeled analogue is at least one of GSH* (Glutathione-(glycine-$^{13}C_2$, $^{15}N$), Cys*(L-Cysteine-$^{13}C_3$, $^{15}N$) Cys**(L-Cysteine-$^{13}C_3$, D3, $^{15}N$), Cystine*(L-Cystine-$^{13}C_6$, $^{15}N_2$), NAC* (L-Cysteine-$^{13}C_3$, $^{15}N$, N-acetyl), Hcy-d4, NEMd5: N-ethylmaleimide (ethyl-D5), GSSG*(disulfide bound Glutathione-(glycine-$^{13}C0_2$, $^{15}N$), NAC*ss, Hcy*ss, Cys*-ss-GSH* (Cys* disulfide bound to GSH*), Cys*-ss-NAC*, Cys**-ss-Hcyd4, Cys*-ss-CG, Cys*-ss-γEC, CG-NEMd5(CysGly alkylated with N-ethylmaleimide (ethyl-D5)), γEC-NEMd5.

In various embodiments of the above aspects, the reagent o prevent free thiol oxidation sample is N-ethylmaleimide (NEM).

In various embodiments of the above aspects, the reagent to prevent free thiol oxidation sample is supplied in a dried form in the sample collection container.

In various embodiments of the above aspects, the amount of the oxidized and reduced forms of thiols: GSH, GSSG, cysteine, cystine, N-acetyl-cysteine (NAC), N-acetyl-cystine, CysGly, gamma-GluCys, homocysteine, Cys-ss-GSH, Cys-ss-NAC, Cys-ss-CysGly, Cys-ss-γGluGys, and Cys-ss-Hcy are measured simultaneously in one assay run.

In various embodiments of the above aspects, the optimized MRM transitions are as shown in Table 1.

In various embodiments of the above aspects, the level of the oxidized forms of thiol and disulfide containing molecules in a sample is at least 1.1, 1.2, 1.3, 1.4, 1.5, 1.6, 1.7, 1.8, 1.9, or 2.0 times the level in the control sample.

In various embodiments of the above aspects, the level of protein-ss-Cys is determined, and a greater amount of protein-ss-Cys in the sample as compared to a control is indicative of oxidative stress in a subject from which the sample was obtained.

In various embodiments of the above aspects, the level of total cysteine is determined, and a greater amount of total cysteine in the sample as compared to a control is indicative of oxidative stress in a subject from which the sample was obtained.

In various embodiments of the above aspects, if a greater amount of oxidized forms of thiol and disulfide containing molecules as compared to a control is determined in the sample, the subject is administered an antioxidant treatment. In various embodiments of the above aspects, the antioxidant treatment is the administration of N-acetyl cysteine. In various embodiments of the above aspects, the administration of N-acetyl cysteine is for 1, 2, 3, or more hours at 75 mg/kg, 150 mg/kg or 300 mg/kg by i.v. infusion. In various embodiments of the above aspects, the administration of N-acetyl cysteine is by oral administration.

In a third aspect, disclosed herein is a kit for performing the aspects and embodiments disclosed above.

In a fourth aspect, disclosed herein is a sample collection container comprising a dried reagent to prevent free thiol oxidation. In some embodiments of this aspect, the container is a vacutainer tube. In some embodiments of this aspect, the reagent to prevent free thiol oxidation is NEM. In some embodiments of this aspect, the NEM is an evenly coated amount of 2-4 mg on the walls of a 1 ml tube.

DETAILED DESCRIPTION

Figure 1:
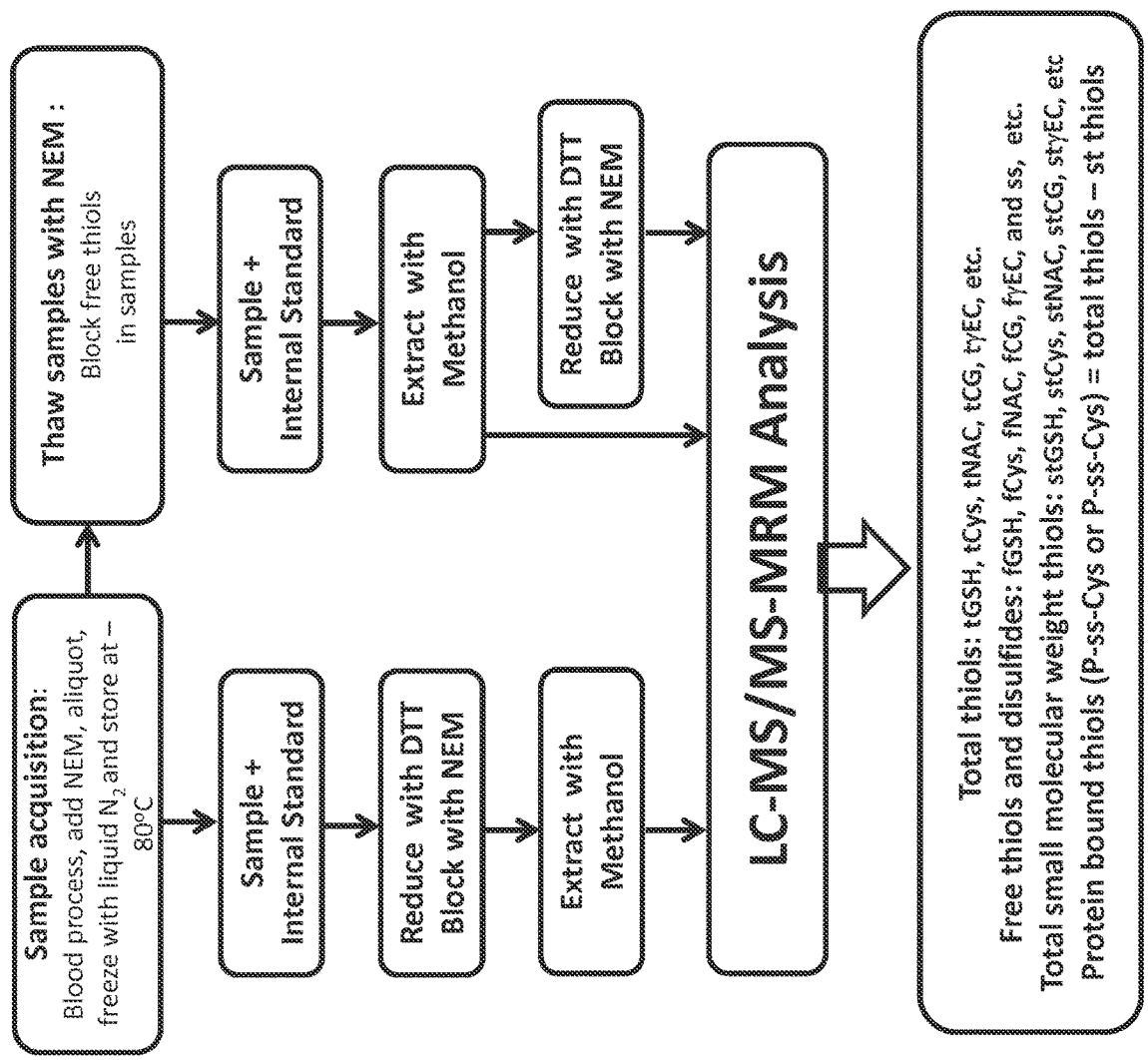
FIG. 1 shows a schematic of the procedures for the analysis of small molecule thiols and disulfides, total thiols, and protein bound thiols.

The present invention generally relates to compositions and methods for determining the level of thiol and disulfide containing molecules in a sample. Furthermore, the compositions and methods can be used to determine oxidative stress in a patient.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

An "analyte" or "target" refers to a compound to be detected. Such compounds can include small molecules, peptides, proteins, nucleic acids, as well as other chemical entities. In the context of the present invention, an analyte or target will generally correspond to the small molecular thiols and disulfides as disclosed herein.

The term "biomarker" refers to a molecule (typically small molecule, protein, nucleic acid, carbohydrate, or lipid) that is expressed and/or released from a cell, which is useful for identification or prediction. Such biomarkers are molecules that can be differentially expressed, e.g., overexpressed or underexpressed, or differentially released in response to varying conditions (e.g., oxidative stress in the present disclosure). In the context of the present invention, this generally refers to thiol and disulfide containing molecules as disclosed herein, which are altered in a patient versus a control, for instance, 1-fold, 2-fold, 3-fold, 4-fold, 5-fold or more in a patient suffering from oxidative stress versus a normal individual.

As used herein, "oxidative stress" refers to an imbalance between generation of reactive oxygen species and antioxidative capacity of biological system. Examples of conditions that result in oxidative stress include: cancer, neurodegenerative disease, cardiovascular disease, sickle cell disease, thrombotic thrombocytopenic purpura (TTP), sepsis, acute respiratory distress syndrome (ARDS), and other inflammatory diseases.

A "sample" refers to any source which is suspected of containing an analyte or target molecule. Examples of samples which may be tested using the present invention include, but are not limited to, blood, serum, plasma, urine, saliva, cerebrospinal fluid, lymph fluids, tissue and tissue and cell extracts, cell culture supernantants, among others. A sample can be suspended or dissolved in liquid materials such as buffers, extractants, solvents, and the like. In the context of the present application, a sample is generally a blood sample or a fraction derived therefrom.

As used herein, the term "thiol and/or disulfide containing molecules" is intended to include any type of molecule that includes a "thiol" or —SH group. Such molecules have the capacity to form disulfide bonds with the same or different species of thiol or —SH group containing molecules. The thiol or —SH form of the molecule is referred to as the reduced form, whereas the S—S or disulfide form is referred to as the oxidized form. Example of such "thiol and/or disulfide containing molecules" include, but are not limited to: GSH, GSSG, cysteine, cystine, N-acetyl-cysteine (NAC), N-acetyl-cystine, CysGly, gamma-GluCys, homocysteine, as well as mixed disulfides such as Cys-ss-GSH, Cys-ss-NAC, Cys-ss-CysGly. Furthermore, such molecules can be naturally occurring or synthetic.

As used herein, "a reagent to prevent free thiol oxidation" refers generally to any reagent which is capable of reacting with a thiol group to prevent it from forming a disulfide bond. Examples of such reagents include, but are not limited to, various iodoacetamides, maleimides, benzylic halides, and bromomethylketones, which react by S-alkylation of thiols to generate stable thioether products. In one embodiment N-ethylmaleimide (NEM) is used.

"Liquid chromatography-tandem mass spectrometry with multiple reaction monitoring (LC-MS/MS-MRM) refers to a mass spectrometry method, where LC is used for sample introduction and separation of analytes. Mass Spectrometry is used for ion detection based on mass to charge ratio (m/z). In LC, the sample is injected by auto-sampler and forced by a liquid (the mobile phase) through a column that is packed with a stationary phase generally composed of octadecylsityl (C18) particles where the analytes are separated based on their physical and chemical properties. In mass spectrometer, analytes are ionized by electrospray ionization, and separated by MSS analyzer based on mass to charge ratio (m/z). The ion of interest can be selected, fragmented, and detected on second stage mass spectrometer. In multiple reaction monitoring (MRM), a set of product ions are selected for detection. In our methods, we used AB SCIEX QTRAP 6500, a triple quadrupole mass spectrometer. The first quadrupole is used to select the desired ion of interest (parent ion); the parent ion is fragmented in the second quadrupole through collisional induced dissociation; fragmentation(s) (also called product ion) is monitored in the third quadrupole. Due to its high sensitivity and high selectivity, this method has been widely used for quantification of peptides and other small molecules in biological samples.

Samples of blood or a fraction thereof or other cells or tissues from a patient can be compared to a "control" which can be a sample from a normal individual. In some embodiments, the patient is a patient suffering from oxidative stress, and the control is a patient without oxidative stress. Control samples are assigned a relative analyte amount or activity to which sample values are compared. Relevant levels of analyte elevation occur when the sample amount or activity value relative to the control is 110%, more preferably 150%, more preferably 200-500% (i.e., two to five fold higher relative to the control), more preferably 1000-3000% higher.

As used herein, "an antioxidant" refers generally a molecule that inhibits the oxidation of other molecules. A number of antioxidatives are known in the art to occur in food or which are available as dietary supplements. Examples of antioxidants include, but are not limited to: beta-carotene, lutein, lycopene, selenium, vitamin A, vitamin C, vitamin E. In one embodiment, N-acetyl cysteine (NAC) is used.

As used herein, a "therapeutically-effective amount" or "an amount effective to reduce the effects of a disease" or "an effective amount" refers to an amount of a composition that is sufficient to prevent oxidative Stress or to alleviate (e.g., mitigate, decrease, reduce) oxidative stress associated with a disease condition.

It is well known that routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Compositions can be administered in a single dose treatment or in multiple dose treatments on a schedule and over a time period appropriate to the age, weight and condition of the subject, the particular formulation used, and the route of administration.

Figure 2:
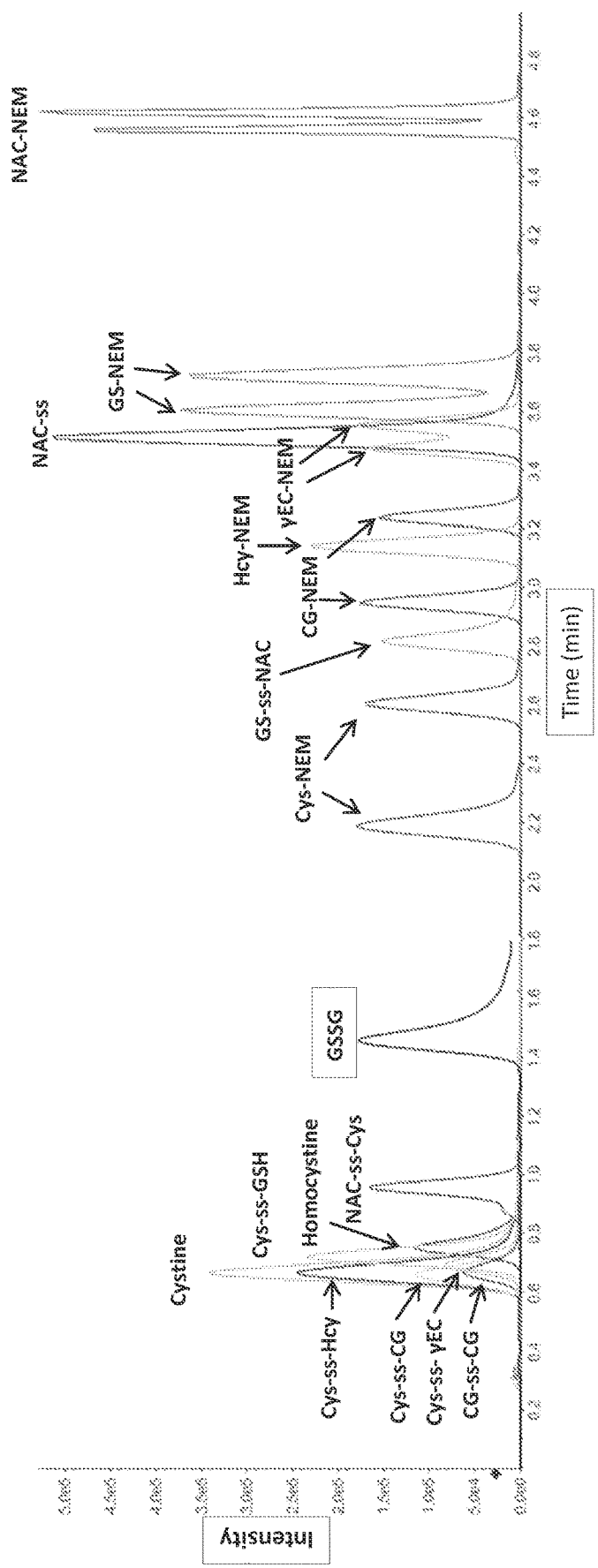
FIG. 2 shows UPLC-MS/MS-MRM detection of selected small molecule thiols and disulfides. Analytes were separated by Waters Ultraperformance Liquid Chromatographer (UPLC) using Waters Cortecs UPLC C18 Column prior to injection on the mass spectrometer. Because they have identical chemical properties isoptically labeled standards coelute with non-labeled analytes. All analytes can be detected simultaneously with a single injection.

Overview of method: Disclosed herein is a liquid chromatography-mass spectrometry (LC-MS) based assay to quantify directly not only the GSH and GSSG and other small molecule free thiols/disulfides, but also protein bound thiols in biological samples including blood, plasma, cells and other tissue samples. These analytes include GSH, cysteine, homocysteine, N-acetyl-cysteine, CysGly, gamma-GluCys, as well as their homo- and mixed disulfides such as GSSG, cystine, N-acetyl-cystine (NAC), Cys-ss-GSH and Cys-ss-NAC mixed disulfides and protein bound thiols such as p-ss-Cys, p-ss-GSH, p-ss-NAC, etc. In this method (FIG. 1), we first react free thiols with N-ethylmaleimide (NEM) to prevent free thiol oxidation during sample processing and analysis [3]. We next mix NEM treated samples with a mixture of internal standards containing an isotopically labeled homologue of each analyte of interest. Methanol is then added to the samples, simultaneously extracting the analytes and precipitating proteins. Supernatants from the extraction were analyzed by LC-MS/MS-MRM. A Waters ultra-performance liquid chromatography (UPLC) with Cortex C18 column is used to separate all disulfides and thiol-NEM and ABSCiex QTRAP 6500 Mass spectrometer is used for detection of each of the analytes. This approach allows us to accurately quantify a full panel of free thiols, and homo and mixed disulfides (FIG. 2). To determine total small molecular thiols and disulfides in supernatant (st-), we reduce the sample with dithiothreitol (DTT) and then block new thiols with NEM before LC-MS analysis. To determine total thiol (t-) concentration we begin with a new sample aliquot, reduce the sample with DTT, and then block all thiols with NEM before methanol extraction (FIG. 1). Protein bound thiol can be calculated by subtracting total unbound small molecular thiols (st-) from total thiol or by subtracting sum of free and all unbound disulfides from total thiol.

Although particular examples of reagents are listed in the overview above, it will be readily appreciated that other suitable reagents may be used in the practice of the present disclosure. For example, other isotopically labeled standards may be used. Also, other suitable thiol blocking agents or reducing agents (e.g. iodoacetamide, vinylpyridine, tris(2-carboxyethyl)phosphine) may be used to treat the samples prior to LC-MS/MS with Multiple Reaction Monitoring (MRM).

The advantages of the present method include, but are not limited to:

Quantitative: By using stable isotopically labeled internal standards, we are able to perform accurately quantitative analysis of GSH, GSSG, cysteine, cystine, N-acetyl-cysteine (NAC), N-acetyl-cystine, CysGly, gamma-GluCys, homocysteine, as well as mixed disulfide such as Cys-ss-GSH, Cys-ss-NAC, Cys-ss-CysGly, p-ss-Cys, p-ss-GSH, p-ss-NAC.

High throughput: once sample is prepared, LC-MS analysis takes only 14 minutes.

Minimial artificial oxidation: the disclosed sample processing method has been developed to include an excess of reagent to block free thiols at the first step, minimizing artificial oxidation.

Sample size: only need 20-50 µl of samples for analysis.

In short, the present disclosure provides a new approach using LC-MS/MS-MRM (Selected Reaction Monitoring) to analyze a full panel of small molecule thiols and disulfides simultaneously in whole blood, red blood cells, platelet rich plasma and platelet pool plasma with high selectivity, reproducibility, and sensitivity. This approach can be modified for use with any biological sample. There was no such method available for either research or clinical assay before the present development.

Kits

The invention provides kits comprising reagents produced in accordance with the present disclosure which can be used, for instance, to perform the determinations of thiol and disulfide molecules described above. The article of manufacture comprises a container with a label. Suitable containers include, for example, bottles, vials, and test tubes. The containers can be formed from a variety of materials such as glass or plastic. The containers hold compositions to perform the measurements, described above. One container can be a sample collection container, which contains a suitable amount of a dried reagent to prevent free thiol oxidation as described above. The label on the container indicates that the composition is used for a particular step or application, and can also indicate directions for use, such as those described above.

In some embodiments, the present disclosure provides sample collection tubes for the collection of samples for the measurement of free and oxidized forms of thiol and disulfide containing molecules as described herein. In some embodiments, the sample collection container comprises a dried reagent to prevent free thiol oxidation. For example, the container for blood samples collection can be a vacutainer tube containing a dried reagent to prevent free thiol oxidation, such as NEM. In some embodiments, the NEM is an evenly coated amount of 2-4 mg on the walls of a 1 ml tube.

In some embodiments, the present invention is practiced using computer implementation. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The following examples of specific aspects for carrying out the present invention are offered for illustrative purposes only, and are not intended to limit the scope of the present invention in any way.

EXAMPLES

Example 1

Methods and Materials

Sample Collection

Whole Blood (WB) was drawn into 3.9% Sodium Citrate vacutainers, mixed with NEM in saline to final concentration of 20 mM. Blood was further processed by centrifugation at 4° C. into red blood cells (RBC), platelet rich plasma (PRP) and platelet poor plasma (PPP) as needed. Sample aliquots were snap frozen in liquid nitrogen and stored at −80° C. until analysis.

Sample Preparation

To quantify free thiols and disulfides, aliquots of WB or PPP were incubated with 4 equivalent volumes of additional NEM at a final concentration of 15 mM. NEM in 5 mM phosphate buffer pH 6.5 at 37° C. for 30 min. Samples were then mixed with isotope labeled internal standard mixture at 1:1 (vol/vol) and extracted with methanol (80% final concentration). After vortexing for 1 min and sonicating on ice for 5 min, samples were kept at −20° C. for 1 hr and then centrifuged for 20 min at 4° C. at 20,000×g. Supernatant was diluted in 0.1% formic acid for LC-MS/MS analysis. To determine the total concentration of thiols, including small-molecule thiols, disulfides, and protein bound thiols, we reduced sample with DTT and blocked thiols with NEM before performing methanol extraction. Protein bound thiols (p-) can be determined by subtracting the sum of unbound small-molecule thiols (free and disulfides) from the total.

LC-MS/MS-MRM Analysis

NEM blocked thiols and disulfides were analyzed by LC-MS/MS-MRM using Waters Ultra Performance Liquid Chromatographer (UPLC) coupled with ABSciex QTRAP 6500 mass spectrometer. Analytes were separated on Cortecs column (2.1 mm×100 mm) at flow rate 0.3 ml/min using solvent A 0.1% formic acid in water as solvent A and 100% Acetonitrile with 0.1% formic acid as solvent B. Analytes were eluted by the following gradient: an initial 0.5% B for 1 min, followed by a linear gradient from 0.5% to 25% B over 5 min, and from 25% to 90% B over 2.5 min to wash column and equilibrate for 5 min. All analytes of interest were eluted within 5 min and detected by triple quadrupole spectrometer (ABSciex QTRAP 5600) using a multiple reaction monitoring (MRM) detection method. Precursor and product ions were optimized and are shown in Table 1. Data were collected by Analyst software and analyzed using MultiQuant software. The peak area of sum of product ions for each precursor ion was used for quantification. Concentration of each analyte was calculated by the ratio of peak area of unlabeled analyte to the homologous isotopically labeled internal standard, multiplied by the concentration of the internal standard.

TABLE 1

Optimized MRM transitions (Q1 and Q3)

| Analytes | Q1 | Q3 |
|---|---|---|
| Cystine | 241.0 | 74.0 |
|  | 241.0 | 120.0 |
| Cystine* | 249.1 | 77.0 |
|  | 249.1 | 124.0 |
| Cys-ss-GSH | 427.1 | 298.0 |
|  | 427.1 | 231.1 |
| Cys*-ss-GSH | 434.1 | 305.1 |
|  | 434.1 | 231.2 |
| Cys-ss-CG | 298.1 | 177.0 |
|  | 298.1 | 130.0 |
| Cys*-ss-CG | 302.1 | 177.0 |
|  | 302.1 | 130.0 |
| Cys-ss-Hcy | 255.0 | 134.0 |
|  | 255.0 | 122.0 |
|  | 255.0 | 88.0 |
| Cys**-ss-Hcyd4 | 266.1 | 138.0 |
|  | 266.1 | 129.0 |
|  | 266.1 | 92.0 |
| Cys-ss-NAC | 283.0 | 162.0 |
|  | 283.0 | 164.0 |
| Cys*-ss-NAC* | 291.1 | 166.1 |
|  | 291.1 | 168.1 |
| Cys-ss-rEC | 370.1 | 241.0 |
|  | 370.1 | 152.0 |
| Cys*-ss-rEC | 374.1 | 245.0 |
|  | 374.1 | 152.0 |
| GSSG | 613.2 | 484.1 |
|  | 613.2 | 355.1 |
|  | 307.1 | 231.1 |
|  | 307.1 | 130.1 |
| GSSG* | 619.2 | 490.1 |
|  | 619.2 | 360.9 |
|  | 310.1 | 231.1 |
|  | 310.1 | 130.1 |
| Hcy-ss | 269.1 | 136.0 |
|  | 269.1 | 134.0 |
| Hcy*-ss (d8) | 277.1 | 138.0 |
|  | 277.1 | 140.0 |
| CG-ss | 355.1 | 235.1 |
|  | 355.1 | 177.0 |
| rEC-ss | 499.1 | 241.0 |
|  | 499.1 | 370.0 |
| NAC-ss | 325.1 | 162.0 |
|  | 325.1 | 164.0 |
| NAC*-ss | 333.1 | 166.0 |
|  | 333.1 | 168.0 |
| GS-ss-NAC | 469.1 | 162.0 |
|  | 469.1 | 340.0 |
| GS*-ss-NAC* | 477.1 | 166.0 |
|  | 477.1 | 348.0 |
| Cys-NEM | 247.1 | 126.1 |
|  | 247.1 | 158.0 |
|  | 247.1 | 158.0 |
| Cys*-NEM | 251.1 | 186.0 |
|  | 251.1 | 126.0 |
|  | 251.1 | 158.0 |
| Cys**-NEM | 254.1 | 126.0 |
|  | 254.1 | 158.0 |
|  | 254.1 | 158.0 |
| GSH-NEM | 433.1 | 201.0 |
|  | 433.1 | 304.0 |
| GSH*-NEM | 436.1 | 201.0 |
|  | 436.1 | 307.0 |
| Hcy-NEM | 261.1 | 56.0 |
| Hcy*-NEM | 265.1 | 60.0 |
| CG-NEM | 304.1 | 201.1 |
|  | 304.1 | 212.1 |
| CG-NEMd5 | 309.1 | 206.1 |
|  | 309.1 | 217.1 |
| rEC-NEM | 376.1 | 201.0 |
|  | 376.1 | 247.1 |
|  | 376.1 | 230.0 |
| rEC-NEMd5 | 381.1 | 206.0 |
|  | 381.1 | 252.1 |
|  | 381.1 | 235.1 |
| NAC-NEM | 289.1 | 230.0 |

TABLE 1-continued

Optimized MRM transitions (Q1 and Q3)

| Analytes | Q1 | Q3 |
|---|---|---|
| NAC*-NEM | 289.1 | 201.1 |
|  | 293.1 | 233.0 |
|  | 293.1 | 204.1 |

Example 2

Figure 3:
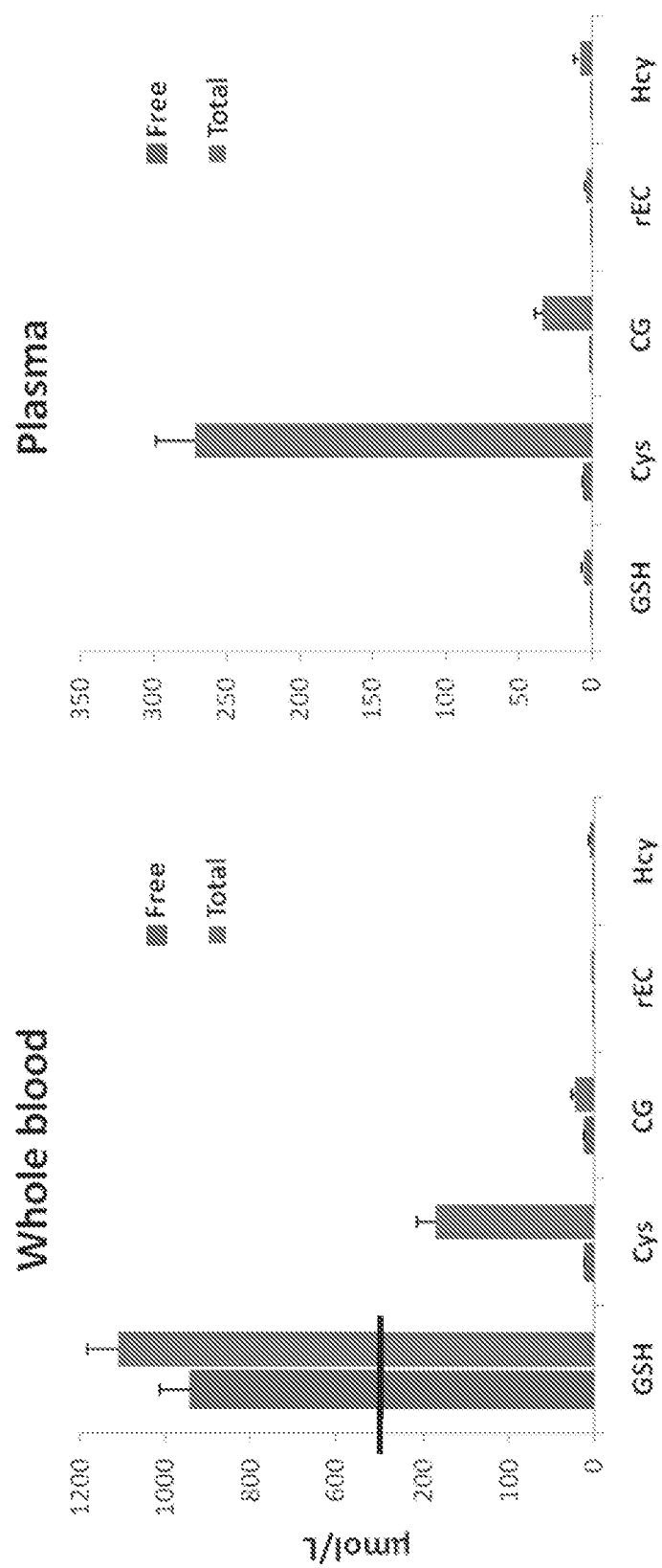
FIG. 3 shows free and total thiol levels in whole blood and plasma from 6 normal healthy donors. Total thiol level is the sum of free and all forms of disulfides including protein bound disulfides. As GSH is an intracellular antioxidant, total concentration reaches over 1 mM and mainly exists in a free form in whole blood, whereas the total concentration of GSH in the plasma is less than 10 µM. In contrast, cysteine, a precursor of GSH is the major thiol species in plasma (over 250 µM) and exists predominantly in oxidized form, as disulfides and mixed disulfides, including as a disulfide with cysteine in plasma proteins.

Analysis of Free and Total Thiols in Whole Blood and Plasma Samples from Normal Healthy Donors FIG. 3 shows the measurements of free and total thiol levels in whole blood and plasma and from six normal healthy donors. Total thiol level is sum of free and all forms of disulfides including protein bound disulfides. As GSH is an intracellular antioxidant, total concentration reaches over 1 mM and mainly exist in a free form in whole blood, whereas the total concentration of GSH in plasma is less than 10 µM. In contrast, cysteine, a precursor of GSH is the major thiol species in plasma (over 250 µM) and exists predominantly in oxidized form, as disulfides and mixed disulfides, including as a disulfide with cysteine in plasma proteins.

Example 3

Figure 4:
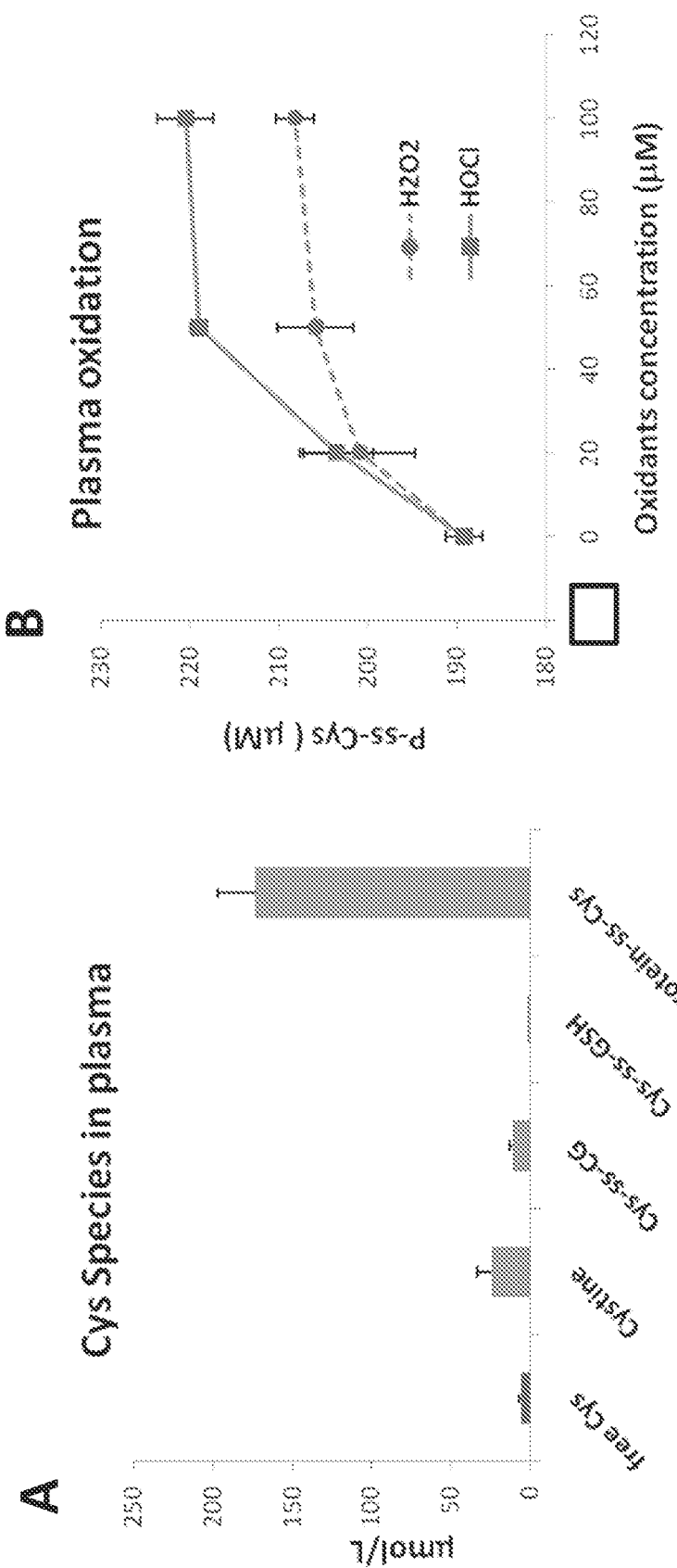
FIG. 4 shows that protein-ss-Cys was increased when plasma is exposed to oxidants in a physiologically relevant concentration range. A. Cys containing species in normal donors' plasma (n=6); B. Plasma from a nomal donor treated with hydrogen peroxide ($H_2O_2$) and hypochlorous acid (HOCl), two oxidants commonly released from activated cells and neutrophils in patients with oxidative stress. Protein-ss-Cys is the most abundant cysteine containing species and is increased with an increase of oxidant concentration, indicating Protein-ss-Cys may serve as a sensitive plasma biomarker for oxidative stress.

Analysis of Protein-ss-Cys in Plasma Treated with Two Physiological Relevant Oxidants FIG. 4 shows that Protein-ss-Cys was increased when plasma is exposed to oxidants in a physiologically relevant concentration range. A. Cys containing species in normal donors' plasma (n=6); B. Plasma from a nomal donor treated with hydrogen peroxide ($H_2O_2$) and hypochlorous acid (HOCl), two oxidants commonly released from activated cells and neutrophils of patients with oxidative stress. Plasma was reaction with the indicated concentration at 37° C. for 30 min and followed by methanol extraction and analysis by LC-MS/MS-MRM as described in Example 1. Protein-ss-Cys is the most abundant cysteine containing species and is increased with an increase of oxidant concentration, indicating that Protein-ss-Cys may serve as a sensitive plasma biomarker for oxidative stress.

Example 4

Figure 5:
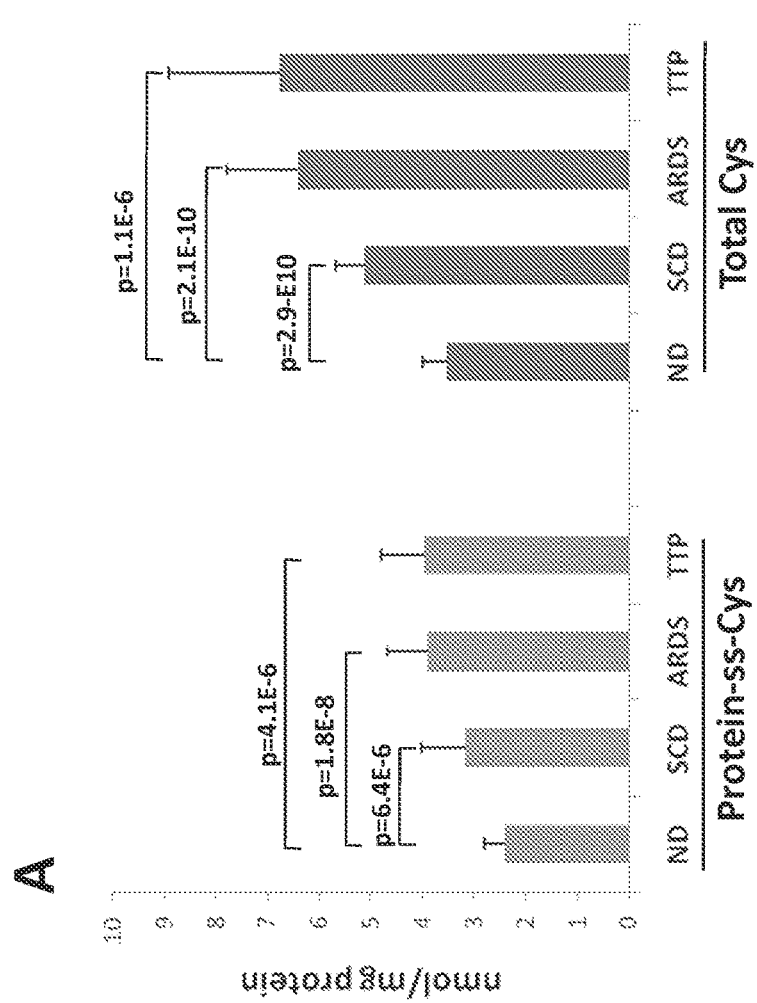
FIG. 5 shows that protein-ss-Cys and total Cys were significantly increased in plasma samples from patients with sickle cell disease (SCD), Acute respiratory distress syndrome (ARDS), and Thrombotic thrombocytopenic purpura (TTP), as compared to normal healthy donors (ND). A. Shows that protein-ss-Cys (p-ss-Cys) and total Cys (t-Cys) in nmol/mg protein were all significantly increased in the plasma from patients with SCD (n=14), ARDS (n=16), and TTP (n=4) compared to ND (n=21). p-value by student T test to normal donors indicated a statistically significant difference between these diseases and normal controls ($p<10^{-5}$), B. Total Cys correlated linearly with protein-ss-Cys. Pearson correlation r=0.84, $p=5.3\times10^{-16}$.

Elevated p-ss-Cys Concentrations and Total Cys were Detected in Samples from Patients with a Rarity of Diseases with Oxidative Stress FIG. 5 shows that protein-ss-Cys and total Cys were significantly increased in plasma samples from patients with sickle cell disease (SCD), Acute respiratory distress syndrome (ARDS), and Thrombotic thrombocytopenic purpura (TTP), as compared to normal healthy donors (ND). A. Shows that protein-ss-Cys (p-ss-Cys) and total Cys (t-Cys) in nmol/mg protein were all significantly increased in the plasma from patients with SCD (n=14), ARDS (n=16), and TTP (n=4) compared to ND (n=21). p-value by student T test to normal donors indicated a statistically significant difference between these diseases and normal controls ($p<10^{-5}$). B. Total Cys correlated linearly with protein-ss-Cys. Pearson correlation r=0.84, $p=5.3 \times 10^{-16}$. These results indicate that either p-ss-Cys or total Cys can be used as a plasma biomarker for oxidative stress.

Example 5

Figure 6:
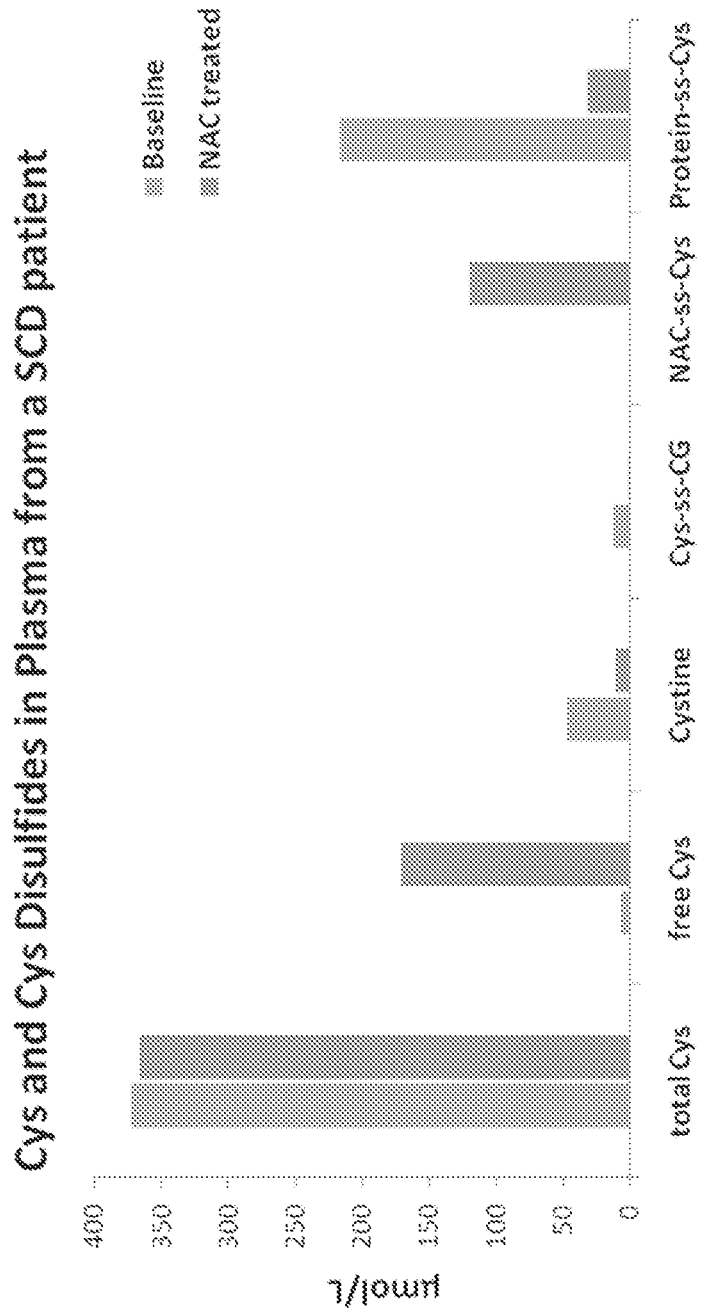
FIG. 6 shows that Cys and Cys disulfide changes in the plasma from a patient before (BL, Baseline) or after infusion of antioxidant drug, N-Acetyl Cysteine for 1 hr at a dose of 150 mg/kg. Although no significant changes were observed for total Cys upon NAC treatment, free Cys was dramatically increased from 7 µM to over 170 µM accompanied with a large decrease of Protein-ss-Cys and Cystine, indicating that NAC rapidly reduced Cys disulfides. Detection of NAC-ss-Cys confirms the role of NAC as an antioxidant to reduce disulfides (oxidized form) to thiol (free) form. Free Cys is an amino acid needed for GSH and protein synthesis.

Analysis of Cys Containing Species in the Plasma from a Patient with SCD Before and After Treatment of N-Acetyl Cysteine (NAC), an Antioxidant Drug SCD patients are known to experience oxidative stress. We have utilized this assay for the SCD NAC clinical trial currently underway at Bloodworks NW Research institute. FIG. 6 illustrates Cys and Cys disulfide changes in the plasma from a patient before (BL, Baseline) or after infusion of an antioxidant drug, N-Acetyl Cysteine for 1 hr at a dose of 150 mg/kg. Free Cys was dramatically increased from 7 µM to over 170 µM accompanied with a large decrease of Protein-ss-Cys and Cystine, indicating that NAC rapidly reduced Cys disulfides. Detection of NAC-ss-Cys confirms NAC as an antioxidant to reduce disulfides (oxidized form) to thiol (free) form. Free Cys is an amino acid needed for GSH and protein synthesis. There were no significant changes observed for total Cys upon NAC treatment, suggesting that the possibility of NAC deacetylation was minor.

Example 6

Figure 7:
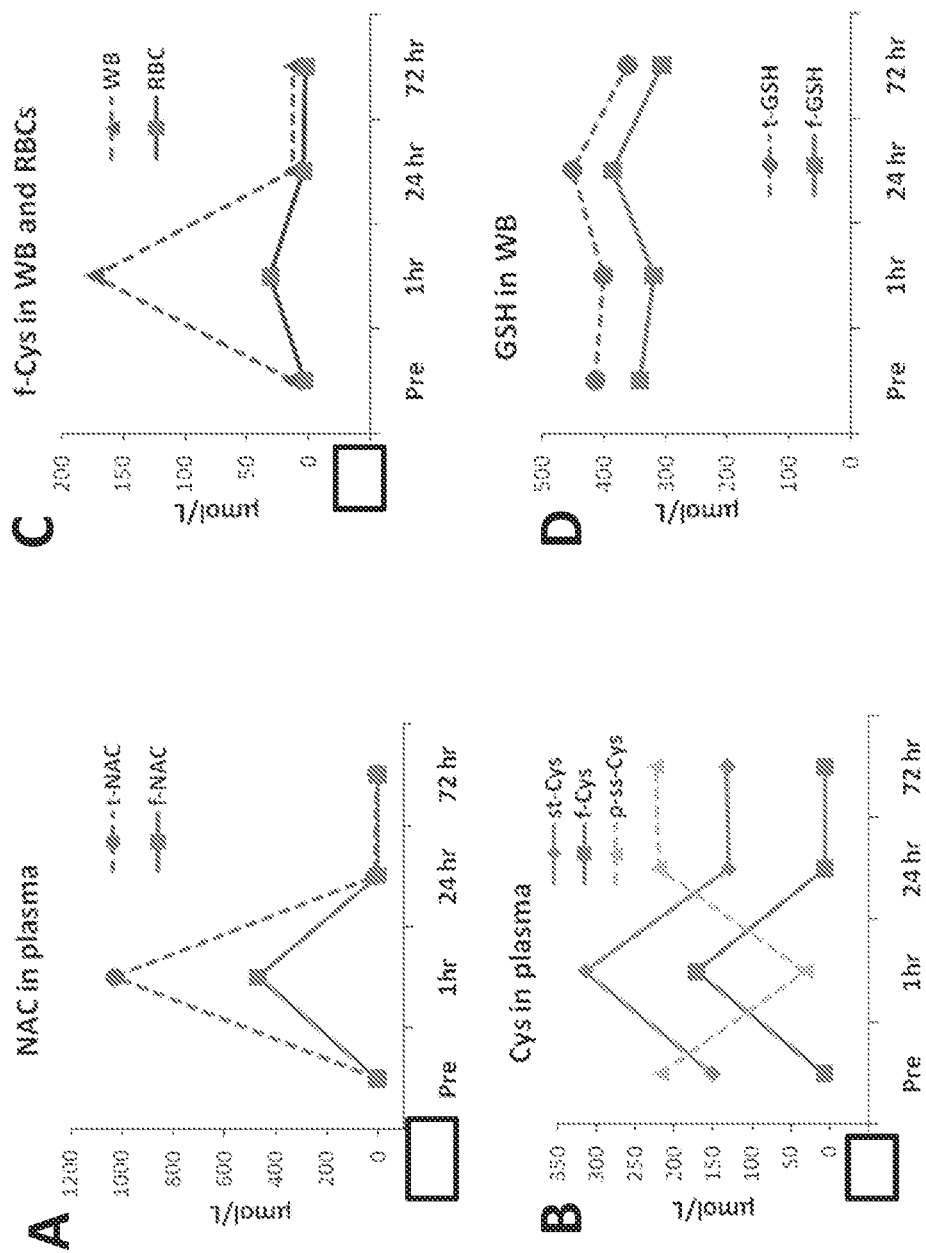
FIG. 7 shows the analysis of NAC, Cys species, and GSH changes in the plasma from a patient before (Pre), right after NAC infusion (1 hr), and at follow up time points (24 hr and 72 hr). Although the NAC drug contained more than 99.5% free NAC, over 50% of NAC was oxidized at 1 hr. NAC was almost not detectable at 24 hr, suggesting a NAC short half time (A). Free Cys and sum of free sys and unbound disulfides (st-Cys) were greatly increased, whereas p-ss-Cys decreased sharply. (B). Free Cys in whole blood is increased from 13 µM to 170 µM and free Cys in the red blood cell (RBC) fraction increased over 10 fold. (C). The increase of free Cys in the RBC fraction likely contributes to GSH synthesis. We observed that GSH level slightly increased (13%) at the 24 hr time point compared to before treatment. SCD patients are known to have lower GSH levels. Total GSH in whole blood (WB) was only about 410 µM, which is less than 40% of the average of normal donors shown in FIG. 3.

Analysis of Time Course of NAC, Cys Containing Species, and GSH in the Plasma/Whole Blood from a Patient with SCD Before and After NAC Treatment FIG. 7 shows NAC, Cys species, and GSH changes in samples from a patient before treatment (Pre), right after NAC infusion (1 hr), and at follow up time points (24 hr and 72 hr). Although the NAC drug contained more than 99.5% reduced free form, over 50% of the NAC was oxidized at 1 hr. NAC was almost not detectable at 24 hr, suggesting NAC had a short half time (A). Free Cys and total small molecular weight thiol (st-Cys) were greatly increased, whereas p-ss-Cys decreased sharply. (B). Free Cys in whole blood is increased from 13 µM to 170 µM and free Cys in the red blood cell (RBC) fraction increased over 10 fold from 2.3 µM to 31 µM. (C). The increase of free Cys in the RBC fraction likely contributes the GSH synthesis. We observed that GSH level slight increased (13%) at 24 hr time point compared to before treatment. SCD patients are known to have lower GSH levels. Total GSH in WB was only about 410 µM, which is less that 40% of average of normal donors shown in FIG. 3.

REFERENCES

1. Rossi, R., et al., *Oxidized Forms of Glutathione in Peripheral Blood as Biomarkers of Oxidative Stress.* Clinical Chemistry, 2006. 52(7): p. 1406-1414.

2. Dalle-Donne, I., et al., *Biomarkers of Oxidative Damage in Human Disease.* Clinical Chemistry, 2006. 52(4): p. 601-623.

3. Rossi. R., et al., *Blood Glutathione Disulfide: In Vivo Factor or in Vitro Artifact?* Clinical Chemistry, 2002. 48(5): p. 742-743.

4. Rossi, R., et al., *Oxidized forms of glutathione in peripheral blood as biomarkers of oxidative stress.* Clin Chem, 2006. 52(7): p. 1406-14.

5. Dalle-Donne, I., et al., *Molecular Mechanisms and Potential Clinical Significance of S-Glutathionylation*, Antioxidants and Redox Signaling, 2008. 10(3): p. 445-473.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A method for measuring the total Cysteine (Cys) level in a sample, the method comprising:
    obtaining a sample comprising Cys containing molecules comprising free Cys and oxidized Cys;
    blocking free Cys oxidation in the sample by adding a blocking reagent to the sample to create a blocked Cys sample;
    adding an isotopically labeled Cys analogue to the blocked Cys sample to create a mixed Cys sample;
    reducing the oxidized Cys to free Cys by adding dithiothreitol (DTT) to the mixed Cys sample to create a reduced mixed Cys sample;
    blocking the free Cys within the reduced mixed Cys sample by adding the blocking reagent to the reduced mixed Cys sample to create a blocked mixed Cys sample;
    extracting blocked Cys from the blocked mixed Cys sample by adding methanol to the blocked mixed Cys sample to create a supernatant containing blocked Cys; and
    subjecting the supernatant containing blocked Cys to liquid chromatography-tandem mass spectrometry (LC-MS/MS) with Multiple Reaction Monitoring (MRM),
    thereby measuring the total Cys level in the sample.

2. The method of claim 1, wherein the sample is plasma, whole blood, cells, or tissue.

3. The method of claim 1, wherein the isotopically labeled Cys analogue is L-Cysteine-$^{13}$C3,$^{15}$N (Cys*).

4. The method of claim 1, wherein the sample is fresh or previously frozen.

5. The method of claim 1, wherein the blocking reagent is N-ethylmaleimide (NEM).

6. The method of claim 1, wherein the total Cys level in the sample is compared to a corresponding total Cys level in a control sample from a normal healthy donor or from an average value derived from samples of healthy donors.

7. The method of claim 1, further measuring the total small molecule Cys level in the sample comprising:
    obtaining an aliquot from the mixed Cys sample to create a mixed Cys aliquot;
    precipitating protein bound Cys (p-ss-Cys) from the mixed Cys aliquot by adding methanol to the mixed Cys aliquot to create an extract of the mixed Cys aliquot without p-ss-Cys;
    reducing the oxidized Cys to free Cys by adding dithiothreitol (DTT) to the extract to create a reduced mixed Cys extract;
    blocking the free Cys within the reduced mixed Cys extract by adding the blocking reagent to the reduced mixed Cys extract to create a blocked mixed Cys extract; and
    subjecting the blocked mixed Cys extract to liquid chromatography-tandem mass spectrometry (LC-MS/MS) with Multiple Reaction Monitoring (MRM), thereby further measuring the total small molecule Cys level in the sample.

8. The method of claim 7, wherein the total small molecule Cys level in the aliquot is compared to a corresponding total small molecule Cys level in a control sample from a normal healthy donor or from an average value derived from samples of healthy donors.

9. A method for determining oxidative stress in a subject, the method comprising measuring the total Cysteine (Cys) level in a sample derived from a subject comprising:
    obtaining a sample comprising Cys containing molecules comprising free Cys and oxidized Cys;
    blocking free Cys oxidation in the sample by adding a blocking reagent to the sample to create a blocked Cys sample;
    adding an isotopically labeled Cys analogue to the blocked Cys sample to create a mixed Cys sample;
    reducing the oxidized Cys to free Cys by adding dithiothreitol (DTT) to the mixed Cys sample to create a reduced mixed Cys sample;
    blocking the free Cys within the reduced mixed Cys sample by adding the blocking reagent to the reduced mixed Cys sample to create a blocked mixed Cys sample;
    extracting blocked Cys from the blocked mixed Cys sample by adding methanol to the blocked mixed Cys sample to create a supernatant containing blocked Cys; and
    subjecting the supernatant containing blocked Cys to liquid chromatography-tandem mass spectrometry (LC-MS/MS) with Multiple Reaction Monitoring (MRM),
    wherein an increased total Cys level as compared to a control value of total Cys level is indicative of oxidative stress in the subject.

10. The method of claim 9, wherein the sample is plasma, whole blood, cells, or tissue.

11. The method of claim 9, wherein the sample is from a subject with a disease that results in oxidative stress.

12. The method of claim 9, wherein the sample is from a subject with sickle cell disease (SCD), acute respiratory distress syndrome (ARDS), or thrombotic thrombocytopenic purpura (TTP).

13. The method of claim 9, wherein the isotopically labeled Cys analogue is L-Cysteine-$^{13}$C3,$^{15}$N (Cys*).

14. The method of claim 9, wherein the sample is fresh or previously frozen.

15. The method of claim 9, wherein the blocking reagent is N-ethylmaleimide (NEM).

16. The method of claim 9, wherein the control value of total Cys level is obtained from a normal healthy donor or from an average value derived from samples of healthy donors.

17. The method of claim 9, further comprising:
    measuring the total small molecule Cys level in the sample comprising:

obtaining an aliquot from the mixed Cys sample to create a mixed Cys aliquot;

precipitating protein bound Cys (p-ss-Cys) from the mixed Cys aliquot by adding methanol to the mixed Cys aliquot to create an extract of the mixed Cys aliquot without p-ss-Cys;

reducing the oxidized Cys to free Cys by adding dithiothreitol (DTT) to the extract to create a reduced mixed Cys extract;

blocking the free Cys within the reduced mixed Cys extract by adding the blocking reagent to the reduced mixed Cys extract to create a blocked mixed Cys extract; and subjecting the blocked mixed Cys extract to liquid chromatography-tandem mass spectrometry (LC-MS/MS) with Multiple Reaction Monitoring (MRM), thereby further measuring the total small molecule Cys level in the sample, and calculating a protein bound Cysteine (p-ss-Cys) level by subtracting the total small molecule Cys level from the total Cys level, wherein an increased p-ss-Cys level as compared to a control value of p-ss-Cys level is indicative of oxidative stress in the subject.

18. The method of claim 17, wherein the control value of p-ss-Cys level is obtained from a normal healthy donor or from an average value derived from samples of healthy donors.

19. The method of claim 17, wherein if the p-ss-Cys level is increased as compared to the control value, the subject is administered an antioxidant treatment.

20. The method of claim 9, wherein if the total Cys level is increased as compared to the control value, the subject is administered an antioxidant treatment.

* * * * *